United States Patent [19]

Hofer, Sr. et al.

[11] 4,042,632
[45] Aug. 16, 1977

[54] POLYOXY SULFOXIDES AND SULFONES AS ANTISTATIC AGENTS

[75] Inventors: Kurt Hofer, Sr.; Kurt Hofer, Jr., both of Munchenstein, Switzerland

[73] Assignee: Sandoz Ltd., Basel, Switzerland

[21] Appl. No.: 602,323

[22] Filed: Aug. 6, 1975

Related U.S. Application Data

[63] Continuation-in-part of Ser. No. 508,421, Sept. 23, 1974, abandoned.

[51] Int. Cl.² .......................................... C07C 147/02
[52] U.S. Cl. ............................ 260/607 AL; 106/169; 252/500; 260/2 A; 260/46.5 G; 260/75 S; 260/78 R; 260/67.6 R; 260/69 R; 260/47 ET; 260/77.5 AP; 526/3
[58] Field of Search ................................ 260/607 AL

[56] References Cited

U.S. PATENT DOCUMENTS

| | | | |
|---|---|---|---|
| 3,382,180 | 5/1968 | Priestley et al. | 260/607 A |
| 3,627,845 | 12/1971 | Hickner et al. | 260/607 A |
| 3,758,595 | 9/1973 | Lamberti et al. | 260/607 A |

*Primary Examiner*—Delbert R. Phillips
*Attorney, Agent, or Firm*—Gerald D. Sharkin; Richard E. Vila; Joseph J. Borovian

[57] ABSTRACT

New antistatic compounds of formula

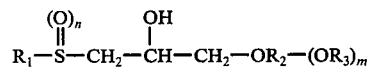

wherein $R_1$ is alkyl optionally interrupted by 1 or 2 S, SO or $SO_2$ moieties or 1 COO moiety, any alkyl(ene) being optionally hydroxyl-substituted; cycloalkyl; alkylcycloalkyl; or a mono- or polyoxyalkylene group terminated by alkyl, optionally alkyl-substituted phenyl or phenylalkyl:, $n$ is 1 or 2;

$m$ is an integer 1 to 7;

$R_2$ is $(m + 1)$ valent alkylene optionally interrupted by 1 or 2 O, S, SO or $SO_2$ moieties; bivalent benzene, cyclohexane, biphenyl, diphenyloxide, -sulphide, -sulphoxide, -sulphone or -methane, 2,2-diphenylpropane, bis-cyclohexylmethane or 2,2-bis-cyclohexylpropane, or a $(m + 1)$ valent mono- or polyoxyalkylene group containing $R_2$;

and each $R_3$, independently, has one of the meanings given for $R_1$, or is hydrogen or phenyl, naphthyl or phenylalkyl optionally substituted on the aromatic nucleus; a group

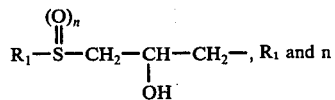 , $R_1$ and $n$ having the above meanings; or a group

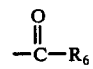

in which $R_6$ is alkyl, perfluoroalkyl or optionally substituted phenyl or naphthyl.

Such compounds are useful as antistatic agents for organic materials, particularly a plastics material such as polypropylene, and may either be incorporated in the organic material directly by admixture therewith or indirectly by admixture with a precondensate thereof and subsequent polymerization, or applied as a coating thereon. They can be produced by processes known per se.

16 Claims, No Drawings

POLYOXY SULFOXIDES AND SULFONES AS ANTISTATIC AGENTS

This application is a continuation-in-part of application Ser. No. 508,421, filed Sept. 23, 1974, now abandoned.

The present invention relates to long chain sulphur containing organic compounds and more specifically to such compounds which, when applied to organic material, reduce the tendency thereof to accumulate static electricity.

The present invention accordingly provides compounds of formula I,

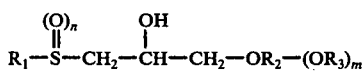

wherein
$R_1$ is alkyl ($C_1$-$C_{22}$) or alkyl ($C_2$-$C_{22}$) containing 1 or 2 alkylenethioalkylene, alkylenesulphinylalkylene or alkylenesulphonylalkylene functions or 1 alkylenecarbonyloxyalkylene function, any alkyl or alkylene being unsubstituted or substituted by —OH; cycloalkyl ($C_5$ or $C_6$) or alkyl ($C_1$-$C_6$) cycloalkyl ($C_5$ or $C_6$); or a radical $-(R_5O)_xR_4$, wherein $R_4$ is alkyl ($C_1$-$C_{22}$), phenyl, phenyl substituted by 1 or 2 alkyl ($C_1$-$C_{12}$) radicals, or phenylalkyl ($C_7$-$C_9$),
each $R_5$ is, independently, —$(CH_2)_2$, —$(CH_2)_3$ or —$CH(CH_3)CH_2$— and $x$ is an integer 1 to 180,
$n$ is 1 or 2,
$m$ is an integer 1 to 7,
$R_2$ is a group $R_{12}$,
wherein
$R_{12}$ is an ($m + 1$) valent saturated aliphatic hydrocarbon ($C_2$-$C_{15}$) radical or an ($m + 1$) valent saturated aliphatic hydrocarbon ($C_2$-$C_{15}$) radical containing 1 or 2 alkyleneoxyalkylene, alkylenethioalkylene, alkylenesulphinylalkylene or alkylenesulphonylalkylene functions; a bivalent radical of benzene, cyclohexane, biphenyl, diphenyloxide, diphenylsulphide, diphenylsulphoxide, diphenylsulphone, diphenylmethane, 2,2-diphenylpropane, bis-cyclohexylmethane or 2,2-bis-cyclohexylpropane, or a group $R_{12}$ $$R_{12}\text{+(OR}_5\text{)}_{\overline{p}}]_q$$

wherein $R_{12}$ and $R_5$ are as defined above, $p$ is an integer 1 to 500, and $q$ is an integer 1 to ($m + 1$), provided that when $q$ is greater than 1, each moiety in square brackets is independent of each other such moiety, and the total number, $y$, of radicals $OR_5$ does not exceed 500, and each $R_3$ has, independently, one of the significances of $R_1$ or is hydrogen, phenyl naphthyl or phenylalkyl ($C_7$-$C_{12}$), or phenyl, naphthyl or phenylalkyl ($C_7$-$C_{12}$) substituted on the aromatic nucleus thereof by 1 to 3 alkyl ($C_1$-$C_{12}$), 1 cycloalkyl ($C_5$ to $C_{12}$), 1 or 2 alkoxy ($C_1$-$C_{18}$), 1 or 2 halogen, 1 phenyl and/or 1 phenoxy substitutent, with 1 to 3 substituents and 1 to 18 carbon atoms in the aggregate thereof, a group

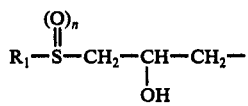

wherein $R_1$ and $n$ are as defined above, or a group

wherein $R_6$ is alkyl ($C_1$-$C_{21}$), perfluoroalkyl ($C_3$-$C_{10}$), phenyl or naphthyl, or phenyl or naphthyl substituted by 1 to 3 halogen, 1 or 2 alkyl ($C_1$-$C_{12}$) or 1 or 2 alkoxy ($C_1$-$C_{12}$) substituents, with 1 to 3 substituents and 1 to 18 carbon atoms in the aggregate thereof with the proviso that the sum of $x$ and $y$ is a maximum of 500.

By the term "halogen" as employed herein is meant fluorine, chlorine, or bromine, preferably chlorine.

Examples of primary alkyl radicals are methyl, ethyl, propyl, butyl, pentyl and hexyl.

Examples of secondary alkyl radicals are isopropyl and 2-butyl.

Examples of tertiary alkyl radicals are tertiary butyl and 2-methyl-2-butyl.

Examples of cycloalkyl radicals are cyclopentyl, cyclohexyl, cyclooctyl and cyclododecyl.

Examples of alkylphenyl radicals are o-methyl-phenyl and p-butyl-phenyl.

Examples of phenylalkyl radicals are benzyl and 2-phenylethyl.

Examples of alkoxy radicals are the alkyl-O-analogues of the alkyl radicals listed above.

In the definition of $R_1$ and $R_{12}$, the expression alkyl ($R_1$) or saturated aliphatic hydrocarbon radical ($R_2$) containing 1 or 2 alkyleneoxyalkylene ($R_{12}$ only), alkylenethioalkylene, alkylenesulphinylalkylene or alkylenesulphonylalkylene functions, or 1 alkylcarbonyloxyalkylene ($R_1$ only) function, means that such alkyl or saturated aliphatic hydrocarbon radical is interrupted once or twice by O, S, SO or $SO_2$, and/or once by COO, respectively and appropriately, no two interrupting moieties being in adjacent positions.

Examples of alkyl radicals which may contain the various functions listed above are $C_4H_9$-$S(O)_{\overline{0,1,2}}(CH_2)_{2,3}$— and $C_8H_{17}$-$S(O)_{\overline{0,1,2}}(CH_2)_{\overline{2,3}}$ such as $C_4H_9S$($CH_2)_2$—, $C_4H_9$-$SO$-$(CH_2)_2$, $C_4H_9SO_2$-$(CH_2)_2$ and $C_4H_9S$-$(CH_2)_3$.

When $R_1$ is alkyl, this is preferably alkyl-($C_4$-$C_{18}$), more preferably alkyl ($C_8$-$C_{18}$), especially alkyl ($C_9$-$C_{14}$).

When $R_1$ is alkyl containing the various functions listed above, it is preferably alkylthioalkyl, alkylsulphinylalkyl, alkylsulphonylalkyl or alkylcarbonyloxyalkyl, each with $C_2$-$C_{22}$ in the aggregate thereof, more preferably alkylsulphonylalkyl and alkylcarbonyloxyalkyl, especially alkylcarbonyloxyalkyl.

When $R_1$ is a group $R_4$($OR_5$)$_x$, $R_5$ is preferably —($CH_2$)$_2$, $x$ is preferably 1 to 100, more preferably 1 to 20, e.g. 1 to 6 and/or $R_4$ is preferably phenyl or phenyl substituted by 1 or 2 alkyl ($C_1$-$C_{12}$) groups, more preferably by 1 or 2 alkyl ($C_1$-$C_9$) groups.

Preferably $R_1$ is alkyl ($C_1$-$C_{22}$), hydroxyalkyl-($C_1$-$C_{22}$), alkylcarbonyloxyalkyl ($C_3$ to $C_{22}$) or $R'_4(OC_2H_4)_{x'}$— wherein $R'_4$ is phenyl or phenyl substituted by 1 or 2 alkyl ($C_1$-$C_9$) groups and $x'$ is an integer 1 to 20.

When $R_2$ is a saturated aliphatic hydrocarbon radical, this is preferably of 2 to 10 carbon atoms, more preferably of 2 to 6 carbon atoms, especially $-(CH_2)_2-$.

Preferably when $R_2$ is a saturated aliphatic hydrocarbon radical, this is an alkylene radical.

When $R_2$ is a saturated aliphatic hydrocarbon radical containing the various functions listed above, this is preferably alkyleneoxyalkylene, alkylenethioalkylene, alkylenesulphinylalkylene or alkylenesulphonylalkylene, especially alkylenesulphonylalkylene. Preferably such radicals are divalent radicals.

When $R_2$ is a group

preferably the total number, $y$, of radicals $OR_5$ is an integer 1 to 300, more preferably 1 to 140, e.g. 1 to 100, especially 1 to 25, particularly 5 to 25. Preferably $R_5$ is $-CH_2-_2$.

Preferably $R_2$ is alkylene $(C_2-C_{10})$, alkylenesulphonylalkylene $(C_2-C_{10})$, a tetravalent neopentane radical, 4,4′-diphenylsulphone, 4,4′-(2,2)-diphenyl propane, 4,4′-(2,2)-bis-cyclohexyl propane or $R_5$−$(OR_5)$−$_6$; more preferably, $R_2$ is divalent alkylene $(C_2-C_{10})$, alkylenesulphonylalkylene $(C_2-C_{10})$, 4,4′-diphenylsulphone, 4,4′-(2,2)-diphenyl propane or $R_5(OR_5)_{y'}$, wherein $R_5$ is as defined above and is preferably $-CH_{2-2}$ and $y'$ is an integer 1 to 300, more preferably 1 to 140, e.g. 1 to 100, especially 1 to 25, particularly 5 to 25.

Particularly preferred significances of $R_3$ are hydrogen, alkyl $(C_1-C_{22})$, phenyl, phenyl substituted by 1 or 2 alkyl $(C_1-C_9)$ groups, a radical

particularly when $R_6$ is alkyl $(C_1-C_{22})$, perfluoroalkyl $(C_3-C_{10})$, phenyl or phenyl substituted by alkyl or chlorine, and a group

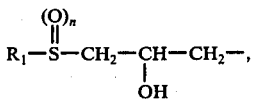

particularly when $R_1$ is $R'_1$, i.e. alkyl $(C_4-C_{18})$, alkylthioalkyl $(C_4-C_{18})$, alkylsulphinylalkyl $(C_4-C_{18})$, alkylsulphonylalkyl$(C_4-C_{18})$ or alkylcarbonyloxyalkyl $(C_5-C_{19})$, any of which is either unsubstituted or substituted by $-OH$; or a radical $-(R_5O)_{x'}R'_4$ wherein $R_5$ is as defined above, $R'_4$ is alkyl $(C_1-C_{22})$, benzyl, phenyl or alkyl $(C_1-C_9)$-phenyl and $x'$ is an integer 1 to 100.

Unless otherwise indicated, any alkyl or alkyl-containing (e.g. alkoxy) radical or alkylene chain may be straight or branched chain.

A preferred class of compounds of formula I are the compounds of formula Ia,

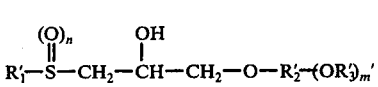

Ia wherein
  $R'_1$ is as defined above,
  $n$ is as defined above,
  $m'$ is an integer 1 to 5,
  $R'_2$ is an $(m' + 1)$ valent saturated aliphatic hydrocarbon $(C_2-C_{10})$ radical, an $(m' + 1)$ valent alkylenesulphonylalkylene $(C_2-C_{10})$ radical, 4,4′-diphenylsulphone, 4,4′-(2,2)-diphenyl propane, i.e.

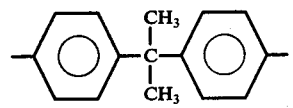

or a radical $-R_5(OR_5)_y-$ wherein $R_5$ is as defined above, and $y'$ is an integer 1 to 300, and each $R'_3$ has, independently, one of the significances of $R'_1$ or is hydrogen, phenyl or benzyl, phenyl or benzyl substituted on the phenyl nucleus by 1 or 2 alkyl $(C_1-C_9)$ or 1 alkoxy $(C_1-C_{18})$ substituted, a group

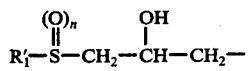

wherein $R'_1$ and $n$ are as defined above, or a group

wherein $R'_6$ is alkyl $(C_9-C_{17})$, phenyl or phenyl substituted by alkyl $(C_1-C_9)$ or chlorine, with the proviso that the sum of $x'$ and $y'$ is a maximum of 300.

A further preferred group of compounds of formula I are the compounds of formula Ib,

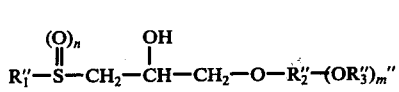

Ib wherein
  $R_1''$ is alkyl $(C_8-C_{18})$,
  $n$ is as defined above,
  $m''$ is an integer 1 or 2
  $R_2''$ is a divalent or trivalent saturated aliphatic hydrocarbon $(C_2-C_6)$ radical or a group $-CH_2CH_2-(OCH_2CH_2)_{y''}-$ wherein $y''$ is an integer 1 to 100 and each
  $R_3''$ is, independently, hydrogen, alkyl $(C_8-C_{18})$ or a group

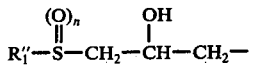

wherein $R_1''$ and $n$ are as defined above.

A further preferred group of compounds within the scope of formula I are the compounds of formula Ic, Ic -continued

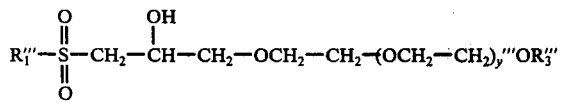

wherein
$R_1'''$ is alkyl ($C_9$-$C_{14}$),
$R_3'''$ is hydrogen or a group

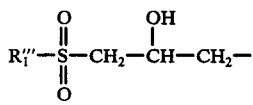

wherein $R_1'''$ is as defined above and $y'''$ is an integer 5 to 25.

A further preferred group of compounds of formula I are the compounds of formula Id,

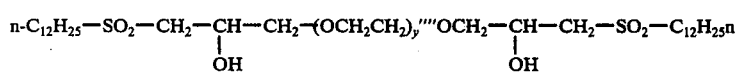

wherein $Y''''$ is an integer 2 to 140.

A further preferred group of compounds of formula I are the compounds of formula Ie,

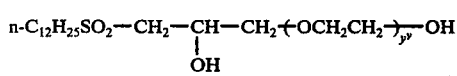

wherein $y^v$ is an integer 20 to 25.

A further preferred group of compounds of formula I are the compounds of formula If,

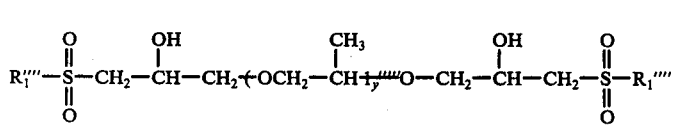

wherein $R''''$ is alkyl ($C_4$-$C_{18}$) and $y'''''$ is an integer 1 to 20.

A further preferred group of compounds of formula I are the compounds of formula Ig,

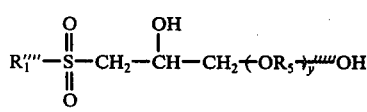

wherein $R_1''''$ is alkyl ($C_4$-$C_{18}$), each $R_5$, independently, is $+CH_2+_2$, $+CH_2+_3$ or $-CH(CH_3)CH_2 13$, and $Y'''''$ is an integer 1 to 20.

The present invention also provides a process for producing a compound of formula I, which comprises
a. condensing a compound of formula II,

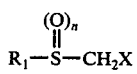

II wherein $R_1$ and $n$ are as defined above and X is a group

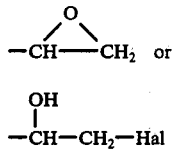

or

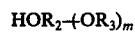

wherein Hal is chlorine or bromine, with a compound of formula III, $$HOR_2 + OR_3)_m \quad\quad III$$

wherein $R_2$, $R_3$ and m are as defined above,
b. condensing a compound of formula IV, $$R_1SO_2H \quad\quad IV$$

wherein $R_1$ is as defined above, with a compound of formula V, $$X-CH_2-O-R_2+OR_7)_m \quad\quad V$$

wherein $R_2$, X and $m$ are as defined above and $R_7$ has one of the significances of $R_3$ or is a group $X-CH_2-$

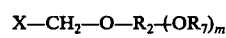

wherein X is as defined above, to produce a compound of formula Id,

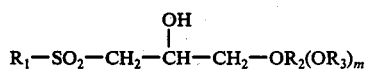

wherein $R_1$, $R_2$, $R_3$ and m are as defined above,
c. selectively oxidising the thio linkage of $R_1$-S-$CH_2$ and, if desired, any in $R_1$, $R_2$ and/or $R_8$ of a compound of formula VI,

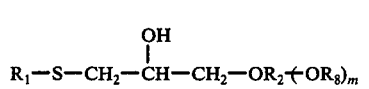

VI wherein $R_1$, $R_2$ and $m$ are as defined above, and $R_8$ is $R_3$ or a group $R_1-S-CH_2CH(OH)CH_2-$, $R_3$ being as defined above, or
d. partially or fully esterifying the terminal hydroxyl group(s) of a compound of formula I, as given and defined above, and in which at least one $R_3$ is hydrogen, with an acid of formula VII,

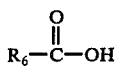

VII wherein $R_6$ is as defined above, or a reactive functional derivative thereof, to produce the corresponding compound of formula I in which at least one $R_3$ is a group

The process in accordance with variant a) may be effected in known manner (e.g. Houben-Weyl, 4th Edition, Vol. 6, part 3, pages 461–464 and Vol. 9, page 134). Thus the reaction may conveniently be effected in aqueous medium, e.g. water or an aqueous hydrocarbon such as aqueous toluene or in the absence of a solvent when the starting materials are liquid. The reaction is preferably effected under either acid or basic conditions. As will be appreciated, the acidity or basicity of the reaction mixture may determine the significance of the group X of formula II. Thus, in alkali medium the compound of formula II, wherein X is a halohydrin function, is converted to the compound wherein X is an epoxide function. Examples of suitable acids are mineral acids such as sulphuric acid or strong Lewis acids, such as boron trifluoride etherate. Examples of suitable bases are alkalis such as sodium or potassium hydroxide. The reaction temperature is suitably in the range 80° to 140° C, conveniently under reflux e.g. at 100° C.

Working up is effected in conventional manner.

The process in accordance with variant (b) may be effected in known manner (e.g. Houben-Weyl, 4th Edition, Vol. 6, part 3, page 458). Thus, the process may be effected in analogous manner to that described above in relation to process variant (a). The reaction is preferably effected under acid conditions. This variant is particularly suitable for the production of compound of formula I, wherein $R_1$ and/or $R_2$ are aromatic radicals.

The process in accordance with variant (c) may be effected in known manner (e.g. Houben-Weyl, 4th Edition, Vol. 9, page 211 et seq and 227 et seq). Thus, selective oxidation may be effected with a peroxide, especially hydrogen peroxide. As will be appreciated, the amount of oxidizing agent and also the reaction conditions employed will determine the oxidation state of the thio linkage(s) in the resulting product. Thus, lower temperatures, e.g. in the range 20° to 25° and one equivalent of hydrogen peroxide favour the lower oxidation state whereas higher temperatures, e.g. 55° to 65° and at least 2 equivalents of hydrogen peroxide favour the higher oxidation state. The reaction with hydrogen peroxide is conveniently effected under acid conditions, e.g. in the presence of sulphuric acid. The oxidation may be effected in conventional solvents, such as hydrocarbon solvents, e.g. toluene.

Working up may be effected in conventional manner.

The process in accordance with variant (d) may be effected under conventional esterification conditions. Thus, for example, the reaction may be effected in conventional solvents such as hydrocarbon solvents, e.g. toluene, in the presence of an acid or base catalyst when the free acid form of the compound of formula VII is employed. When the compound of formula VII is in acid chloride form, preferably the reaction is effected in the presence of an acid acceptor. The reaction temperature is suitably in the range 40° to 100° C.

Working up may be effected in conventional manner.

The compounds of formula II employed as starting material in process variant (a) may be produced a' by condensing a compound of formula IV with a compound of formula VIII,

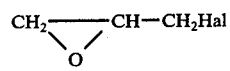 VIII wherein Hal is as defined above, to produce a compound of formula IIa,

 IIa wherein $R_1$ and X are as defined above, or b' by selectively oxidizing the thio linkage of $R_1$—S—$CH_2$ and, if desired, any in $R_1$ of a compound of formula IX,

 IX wherein $R_1$ and X are as defined above.

The process in accordance with variant (a') may be effected in analogous manner to that described in relation to variant (a) above.

The process in accordance with variant (b') may be effected in analogous manner to that described in relation to variant (c) above.

The compound of formula IX, may be produced by condensing a compound of formula X,

 X wherein $R_1$ is as defined above, with a compound of formula VIII, in analogous manner to that described in relation to process variant (a') above.

Examples of readily available compounds of formula III are ethylene glycol, diethylene glycol, triethylene glycol polyethylene glycols with molecular weights of 200 to approximately 20,000 and also their monoethers, 1,2-propylene glycol, dipropylene glycol, tripropylene glycol, polypropylene glycols with molecular weights of 200 to approximately 20,000 and also their monoethers, 1,3-dihydroxypropane, 1,2-, 1,3- 2,3- and 1,4-butandiol, 1, 2, 4 butantriol, 1,6-hexandiol, 1,2,6-hexantriol, 1, 10-decandiol, thiodiglycol, glycerine, diglycerine, polyglycerine, neopentylglycol, pentaerythritol, dipentaerythritol, tripentaerythritol, sorbitol, also their partial etherification products and also their reaction products with ethylene oxide and/or propylene oxide, cyclohexandiol, resorcinol, hydroquinone, 4,4'-dihydroxy biphenyl, 4,4'-dihydroxy diphenyl ether, -sulphide, -sulphoxide, -sulphone,-methane,-isopropane and also the hydrogeneration products of the two last mentioned compounds; also the monoethers or esters with radicals, as described under $R_3$. Also suitable are polyglycol ethers which simultaneously contain ethylene glycol and 1,2 propylene glycol radicals and also their monoethers. Examples of these are $C_4H_9$—O—$C_2H_4$—O—$C_2H_4$—OH, n—$C_{12}H_{25}$— $(OC_2H_4)_8$OH, i-$C_{13}H_{27}$—$(OC_2H_4)_w$OH, wherein $w = 6 - 60$, preferably 12 – 40,

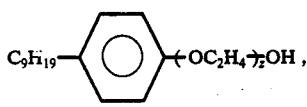

wherein z = 8 to 80, preferably 12 – 40,

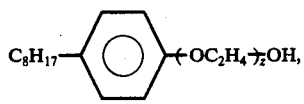

wherein z is as defined above and

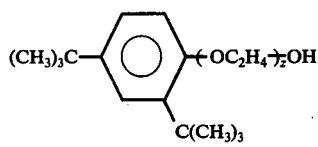

wherein z is as defined above.

The compounds of formula V, employed as starting material in process variant (b) may be produced by condensing a compound of formula III with a compound of formula VIII.

The process may be effected in analogous manner to that described in relation to process variant (a) above.

The compounds of formula VI, employed in process variant (c) may be produced in analogous manner to process variants (a), (b) and (d) above, employing as starting materials the following: for process variant (a), compounds of formulae IX (instead of II) and IIIa,

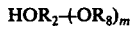  IIIa wherein $R_2$, $R_8$ and m are as defined above; for process variant (b), compounds of formulae X (instead of IV) and Va,

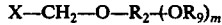  Va wherein $R_2$, X and m are as defined above, and $R_9$ is $R_7$ or a group $R_1$—S—$CH_2$CH(OH)$CH_2$—, $R_1$ and $R_7$ being as defined above; and for process variant (d), compounds of formulae VII and VIa,

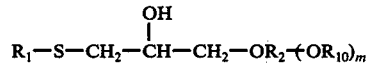  VIa wherein $R_1$, $R_2$ and m are as defined above, and $R_{10}$ is $R_3$ or a group $R_1$—S—$CH_2$CH(OH)$CH_2$—, $R_1$ and $R_3$ being as defined above, at least one $R_{10}$ being hydrogen; the product in this case being of formula VI, wherein at least one $R_8$ in $(OR_8)_m$ is the group

$R_6$ being as defined above.

Where the production of starting materials has not been described, these are either known or may be produced in known manner.

In general, it is not necessary to isolate the starting materials employed in process variants (a), (b), (c) and (d) from the reaction mixture from which they are produced. In addition, and as will be readily appreciated from a consideration of the chemistry involved, the production of compounds of formula I via the process for the production of the starting materials as described above without isolation of the starting material, will often lead to a mixture of compounds of formula I and in certain circumstances also secondary products will be produced. In general, when mixtures of compounds are produced, the antistatic utility thereof is not, or is not unduly, impaired and accordingly separation in such circumstances is not considered necessary. Accordingly, the present invention embraces mixtures of compounds predominantly of formula I as well as the pure compounds of formula I.

It is to be noted in the reactions described above involving the use of a compound of formula VIII that in view of the bifunctionality of this compound, secondary reactions may ensue unless suitable precautions are taken. For example, in the reaction between a compound of formula IV or X with a compound of formula VIII to produce compounds of formula IIa or IX respectively, secondary products such as those of formula XII,

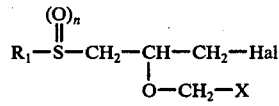  XII wherein $R_1$, n, Hal and X are as defined above, or of formula XIII,

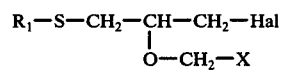  XIII wherein $R_1$, Hal and X are as defined above, may be produced. In such circumstances, it is preferable to employ an excess, e.g. 10 to 30 % molar excess of the compound of formula VIII.

The compounds of formula I are useful for reducing the tendency of organic material to accumulate static electricity by a method comprising treating the organic material with a compound of formula I as antistatic agent. By the term "treating" is meant either surface coating or incorporation into the body of the organic material, in manner known per se. Such treatment serves or also serves, to improve the electrical conductivity of the organic material.

The above method also forms part of the present invention.

The method of the invention comprises treating the organic material, either by way of coating the compound of formula I as a film on the surface of the organic material, or by way of mixing the compound of formula I with the organic material, preferably the latter, so as to uniformly distribute the compound of formula I throughout the body of the organic material. Thus, according to a first embodiment, the method may be effected by intimately mixing the antistatic agent with a particulate form of, for example, a plastics material such as polypropylene, e.g. polypropylene granules, in a kneader or other suitable device, to obtain uniform distribution of the stabilizer throughout the plastics material. The plastics material may thereafter be formed into final shape such as by extrusion into textile filaments or injection moulding. By such method, homogeneous distribution of the antistatic agent throughout the plastics material is achieved which is important for a good and long lasting antistatic effect.

According to a second embodiment of the method of the present invention, particularly suited to the treatment of polymers or copolymers, e.g. polypropylene, the antistatic agent is mixed with the monomer or prepolymer before polymerisation or, as the case may be, copolymerization, is effected, to yield the polymer or copolymer having the antistatic agent uniformly distributed therethrough. The polymer or copolymer may thereafter be extruded, moulded or otherwise formed into final shape, e.g. extruded into textile filaments.

The organic material to be treated may be in liquid form, e.g. liquid hydrocarbons or resins or in solid form, e.g. plastics material. Examples of organic materials susceptible to degradation and embraced by the method of the present invention are especially synthetic polymeric materials such as celluloe derivatives, e.g. cellulose acetate, cellulose acetobutyrate, ethyl cellulose, cellulose nitrate and cellulose propionate, polyalkylenes, notably polyethylene and polypropylene, polyvinyl derivatives, e.g. polyvinyl chloride, polyvinyl acetate and polyvinyl alcohol, polyamides, saturated or unsaturated polyesters, polyacrylonitrile, polystyrene, silicon rubber, melamineformaldehyde resins, urea-formaldehyde resins, allyl casting resins, polymethylmethacrylate, polypropylene oxide, polyphenylene oxide polyurethanes and copolymers such as acrylontrile - butadiene - styrene copolymers. The compounds of formula I that are thermostable are particularly appropriate for treating polyamides, imparting notable antistatic properties even in dry atmospheres.

Antistatically treated organic materials according to the invention may exist in solid form, e.g. panels, rods, coatings, sheets, films, tapes, fibers granules or powders, or in liquor form, e.g. solutions, emulsions or dispersions.

The amount of antistatic agent employed in the method of the present invention will of course vary with the mode of application, the compound employed and the nature of the organic material to be treated. In general, however, satisfactory results are obtained when the amount of agent employed is between 0.05 and 5 %, preferably between 0.5 and 3 % of the weight or organic material to be treated.

The compounds of formula I may be employed in formulation form for the antistatic treatment of solid organic materials, in association with an inert carrier or diluent. Such formulations may be in the form of polishes and varnishes for surface application to the organic material. Such formulations also form part of the present invention.

The compounds of formula I may be employed together with other chemical agents, e.g. heat, oxidation and/or U.V. light stabilizers.

In the following Examples the parts and percentages are by weight and the temperatures in degrees centigrade. The indicated structures are verified by microanalysis and spectroscopic analysis.

EXAMPLE 1 a. 120 Parts by weight of epichlorohydrin are added at approximately 20° - 25° to 202 parts n-dodecyl mercaptan, 300 parts toluene and 160 parts 30 % caustic soda solution with vigorous stirring over the course of approximately 1 hour. Stirring is then continued at the same temperature for 5 hours. The aqueous layer is then separated off, the toluene layer is washed with water and the toluene and some water is distilled off in a vacuum at approximately 40°. This leaves 265 parts of a colorless, clear liquid, mainly of formula A,

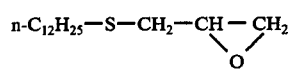
                                    A

Analysis:
Found: S 12.0 %; Cl 0 %;
Calc.: 12.4 %; 0 A%.
Epoxide content: Found: 85 % b. The 265 parts of compound of formula A obtained above are added with stirring at 100° within approximately 1 hour to 300 parts polyethylene glycol (average molecular weight 300) which has been mixed with 5 parts boron trifluoride etherate. Stirring is continued for 2 hours at 100°, the whole is then cooled to 80° and 300 parts hydrogen peroxide (36 %) are allowed to flow in over approximately 30 minutes. After this the temperature is raised to 90° - 92° and stirring is continued at this temperature for 6 hours. The water is then distilled off at approximately 70° under vacuum and the residue is dissolved in 300 parts toluene. It is then cooled and filtered. The filtrate is freed from toluene by vacuum distillation at 50° - 60°. 450 parts of a viscous, colourless liquid is obtained which contains for the main part the compound of formula B $$\text{n-C}_{12}\text{H}_{25}\text{—SO}_2\text{—CH}_2\text{—}\underset{\underset{\text{OH}}{|}}{\text{CH}}\text{—CH}_2\text{—(OC}_2\text{H}_4)_7\text{OH} \qquad B$$

Sulphur content: calculated for $C_{29}H_{60}O_{11}S$: 5.19 %
Found: 5.3 %

If the polyethylene glycol 300 ("300" indicating the average molecular weight) is replaced by equivalent amounts of polyethylene glycols 200, 600, 1000, 1500, 3000 or 6000, glycols having molecular weights 200 and 600 yield viscous colourless liquids, glycols with molecular weights 1000 and 1500 yield soft wax-like masses and glycols with molecular weights 3000 and 6000 yield fairly hard waxes (with melting points above 60° C).

EXAMPLE 2

Example 1 is repeated employing 50 % of the amount of each glycol employed in Example 1. Compounds are obtained which are mainly of the following formula:

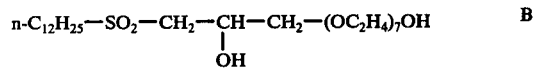

| Glycol used | n | Appearance |
| --- | --- | --- |
| Diethyl glycol | 2 | liquid |
| Polyethylene glycol | 200 approx. 4.5 | viscous |
| Polyethylene glycol | 300 approx. 7 | viscous |
| Polyethylene glycol | 600 approx. 14 | viscous |
| Polyethylene glycol | 1000 approx. 23 | soft wax (melting range ~40° C) |

-continued

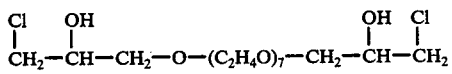

| Glycol used | n | Appearance |
| --- | --- | --- |
| Polyethylene glycol | 1500 approx. 34 | somewhat harder wax (melting range 50°-60° C) |
| Polyethylene glycol | 3000 approx. 68 | hard wax (melting range >60° C) |
| Polyethylene glycol | 6000 approx.136 | hard wax (melting range >60° C) |

EXAMPLE 3

To 12.5 parts thiodiglycol in 50 parts toluene is added 1 part boron trifluoride etherate, followed by 65 parts of compound A from Example 1 at 100° over the course of 30 minutes. The whole is kept at reflux (approximately 100° ) for 2 hours with stirring, then cooled to 80° and 65 parts hydrogen peroxide (36 %) are added over approximately 1 hour. Stirring is then continued for 4 hours at 80° - 85°. After cooling, 2 parts potassium carbonate and 100 parts water are added and the aqueous layer is then separated off. The toluene solution is washed out with water and the toluene is removed by vacuum distillation at 60°. The residue is 60 parts of a white paste consisting mainly of the following compound:

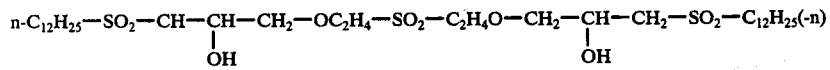

Analysis for $C_{34}H_{70}O_{10}S_3$: Found: S 13.4 %; Calc. 13.08 %.

EXAMPLE 4

The procedure as in Example 3 except that in place of 12.5 parts thiodiglycol, 13.7 parts pentaerythritol are reacted with compound A. 64 Parts of a white hard wax which has a melting range of 80° -105° and which can be readily pulverised are obtained. The compound is principally of the formula

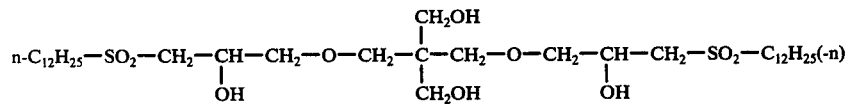

Analysis for $C_{365}H_{72}O_{10}S_2$ found: S, 9.2%; calc.: S, 8.94%.

EXAMPLE 5 a. 30 Parts polyethylene glycol 300 in 50 parts toluene are mixed with 1 part boron trifluoride etherate. 18.5 Parts epichlorohydrin are added dropwise while vigorously stirring, the temperature being maintained at 50°. Stirring is then continued for 4 hours at 60°. After vacuum distillation at 50°, 48 parts of a yellow oil of the following formula are obtained:

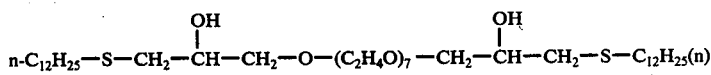

Microanalysis:
Calc.: C, 46.4 %; H, 7.7 %; O 30.7 %; Cl 15.2 %; Found: C, 44.6 %; H, 7.7 %; O 32.8 %; Cl 14.6 %.

b. To 38.8 parts of the product obtained under (a) above and 36.4 parts n-dodecyl mercaptan is added dropwise with vigorous stirring a solution of 11.2 parts potassium hydroxide in 40 parts water over the course of approximately 1 hour. Stirring is then continued for 6 hours at 80°. The product is then taken up in butanol, washed with 10 % caustic soda solution and water and evaporated until dry. 55 Parts of a colourless oil of the following structure are obtained $$\underset{\underset{OH}{|}}{n\text{-}C_{12}H_{25}\text{-}S\text{-}CH_2\text{-}CH\text{-}CH_2\text{-}O\text{-}(C_2H_4O)_7}\text{-}CH_2\text{-}\underset{\underset{OH}{|}}{CH}\text{-}CH_2\text{-}S\text{-}C_{12}H_{25}(n)$$

Microanalysis: Calc: S, 7.8 % Cl, 0 %; Found: S, 9.2 % Cl, 0.4 %.

c. 25 Parts of the product from b) above are dissolved in 60 parts toluene and mixed with 1.5 parts of a 50 % aqueous sulphuric acid. 17 Parts of hydrogen peroxide (at least 30 %) solution are added dropwise at 60° with vigorous stirring over the course of approximately 1 hour. Stirring is continued for 6 hours at 90° - 92°, the surplus hydrogen peroxide is reduced with sodium bisulphite solution, the whole is diluted with toluene and butanol and washed with 10 % caustic soda solution and water. After vacuum distillation at 50° 24 parts of a practically colourless oil of the following structure are obtained

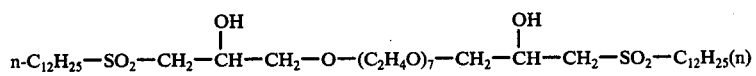

Calc.: C, 58.6 %; H, 10.0 %; O, 23.6 %; S, 7.3 %; Cl, 0 %; Found: C, 38.8 %; H, 10.4 %; O, 22.9 %; S, 7.3 %; Cl, 0.5 %.

If the n-dodecyl mercaptan in stage (b) is replaced by n-butyl mercaptan or mercaptan ethanol, the following final products are obtained respectively

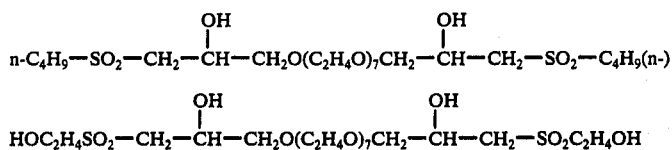

These are colourless, viscous liquids. The latter product can be readily converted into the mono or diester, e.g. by reacting with an acid chloride in the presence of an organic base such as pyridine, triethylamine etc. Thus, by using 2 mols stearic acid chloride, white, odourless wax-like products are obtained.

EXAMPLE 6

The procedure is as in the preceding Examples 5 (a) and 5 (b). During the subsequent oxidation of the dithioether obtained, which is carried out as in Example 5 (c), only 8.5 parts 30% hydrogen peroxide are used in place of 17 parts, and this is added dropwise at 20°–22°. Stirring is continued at this temperature for 48 hours and the process then continues as described in Example 5 (c). 21.5 Parts of a practically colourless, viscous oil which exhibits in the infrared spectrum only a weak $SO_2$ band at 7.75 μ but a strong SO band at 9.7 μ, are obtained. This is principally the disulphoxide of the following formula

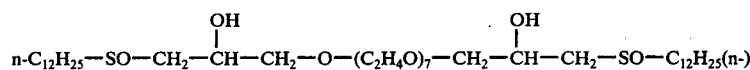

Sulphur content: Calculated: 7.06% S; Found 7.0% S.

EXAMPLE 7

Application

2 Parts of the reaction product according to Example 1 of the compound of formula A with polyethylene glycol 1000, are mixed in a kneader with 98 parts polystyrene and then processed on press to give sheets of 100 × 100 × 1 mm. The surface resistance is then measured using a special measuring cell according to DIN (German Standard) 53482.

The compound produced according to Example 2 from compound A and a polyethylene glycol with a molecular weight of 1000 is then tested in an analogous manner.

EXAMPLE 8

Application

2 Parts of the reaction product according to Example 1 from compound A with polyethylene glycol 1000 and 1500, and according to Example 2 from compound A with polyethylene glycol 1000 and 1500 are separately mixed with 98 parts polycaprolactam and extruded at 240° in the form of a tow. This is then granulated and the granules are processed at 230° on an injection moulding machine into sheets of 100 × 100 × 1 mm. These are then tested in accordance with DIN 53482.

The reaction product according to Example 1 may alternatively be employed in the production of the caprolactam, i.e. at the beginning of the polycondensation thereof, particularly when the polycaprolactam is processed into threads or foils.

The compounds indicated in the following Table are produced in manner analogous to that described in Examples 1 to 6.

| EXAMPLE No.: | Formula |
|---|---|
| 9 | $C_{12}H_{25}SO_2-CH_2-CHOH-CH_2-(OC_2H_4)_{30}OH$ |
| 10 | $C_{13}H_{27}SO_2-CH_2-CHOH-CH_2-(OC_2H_4)_{40}OH$ |
| 11 | $C_8H_{17}SO_2-CH_2-CHOH-CH_2-(OC_2H_4)_7OH$ |
| 12 | $C_{12}H_{25}SO_2-CH_2-CHOH-CH_2-(OC_2H_4)_{13.6}OH$ |
| 13 | $C_{12}H_{25}SO_2-CH_2-CHOH-CH_2-(OC_2H_4)_{23}OCOC_{11}H_{23}$ |
| 14 | $C_{12}H_{25}SO_2-CH_2-CHOH-CH_2-(OC_2H_4)_{40}OCOC_{17}H_{35}$ |
| 15 | $C_{12}H_{25}SO_2-CH_2-CHOH-CH_2-(OC_2H_4)_{10}OCO-\bigcirc\!\!-\!\!+$ |
| 16 | $C_{12}H_{25}SO_2-CH_2-CHOH-CH_2-(OC_2H_4)_{12}OCOC_7F_{15}$ |
| 17 | $C_{12}H_{25}SO_2-CH_2-CHOH-CH_2-(OC_2H_4)_{15}OCO-\bigcirc\!\!-\!\!Cl$ |
| 18 | $C_9H_{19}COOC_2H_4-SO_2-CH_2-CHOH-CH_2-(OC_2H_4)_7OCH_2-CHOH-CH_2-SO_2-C_2H_4OCOC_9H_{19}$ |
| 19 |  |
| 20 | $C_9H_{19}-\bigcirc\!\!-\!\!(OC_2H_4)_5-SO_2-CH_2-CH-CH_2-(OC_2H_4)_5OH$<br>$\qquad\qquad\qquad\qquad\qquad\qquad\qquad\qquad\;\;OH$ |
| 21 | $HO-C_2H_4-SO_2-CH_2-CHOH-CH_2-(OC_2H_4)_{10}-\bigcirc\!\!-\!\!C_9H_{19}$ |
| 22 | $CH_3-SO_2-CH_2-CHOH-CH_2-(OC_2H_4)_{17}-O-C_{18}H_{37}$ |
| 23 | $C_{12}H_{25}-SO_2-CH_2-CHOH-CH_2-(OC_2H_4)_{20}-O-C_{13}H_{27}$ |
| 24 | $C_{12}H_{25}-SO_2-CH_2-CHOH-CH_2-(OC_2H_4)_{60}-O-C_{13}H_{27}$ |
| 25 | $C_{12}H_{25}-SO_2-CH_2-CHOH-CH_2-(OC_2H_4)_{10}-O-\bigcirc\!\!-\!\!C_9H_{19}$ |
| 26 | $C_{12}H_{25}-SO_2-CH_2-CHOH-CH_2-(OC_2H_4)_{15}-O-\bigcirc\!\!-\!\!+$ |
| 27 | $C_{12}H_{25}-SO_2-CH_2-CHOH-CH_2-O-CH_2-CHOH-CH_2-SO_2-C_{12}H_{25}$<br>$\qquad\qquad\qquad\qquad\qquad\qquad\qquad\qquad\quad CH_3$ |
| 28 | $C_{12}H_{25}-SO_2-CH_2-CHOH-CH_2-O-\bigcirc\!\!-\!\!\underset{CH_3}{\overset{CH_3}{C}}\!-\!\bigcirc\!\!-\!\!SO_2-CH_2-CHOH-CH_2-SO_2-C_{12}H_{25}$ |
| 29 | $C_{12}H_{25}-SO_2-CH_2-CHOH-CH_2-O-\bigcirc\!\!-\!\!\underset{CH_3}{\overset{CH_3}{C}}\!-\!\bigcirc\!\!-\!\!O-(C_2H_4O)_5-CH_2-CHOH-CH_2-SO_2-C_{12}H_{25}$ |
| 30 | $C_{12}H_{25}-SO_2-CH_2-CHOH-CH_2-O-\bigcirc\!\!-\!\!\underset{CH_3}{\overset{CH_3}{C}}\!-\!\bigcirc\!\!-\!\!O-CH_2-CHOH-CH_2-SO_2-C_{12}H_{25}$ |
| 31 | $H-\bigcirc\!\!-\!\!SO_2-CH_2-CHOH-CH_2-(OC_2H_4)_{14}-O-CH_2-CHOH-CH_2-SO_2-\bigcirc\!\!-\!\!H$ |

[N.B. $+ = -C(CH_3)_3$]

EXAMPLE 32 a. In an analogous manner to the procedure described in Example 5(a), starting from 256 parts of polypropylene glycol (average molecular weight 1025), 4 parts of boron trifluoride etherate and 46.2 parts of epichlorohydrin and stirring initially at 45° and subsequently for 6 hours at 60°, 300 parts of a yellowish oil of the following formula are obtained:

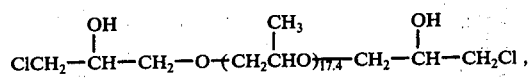

the Fig. 17.4 being an average value for a mixture of products obtained with various numbers of ethyleneoxy repeating units per molecule.

b. From a solution of 60.5 parts of the product of a) above in 100 parts of water, 20.8 parts of n-dodecyl mercaptan and a solution of 5.2 parts of sodium hydroxide in 10 parts of water, through reaction initially at 45° and subsequently at 80° with stirring over a period of 10 hours, 69 parts of a clear, yellowish oil of the formula:

are obtained in an analogous manner to the procedure described in Example 5(b).

c. In an analogous manner to the procedure described in Example 5(c), 30 parts of the product of (b) above are oxidized in the presence of 1.8 parts of formic acid with 3.9 parts of 35% hydrogen peroxide solution at 40° and then at 100°, after addition of a further 7.9 parts of 35% hydrogen peroxide solution, over a period of 6 hours. After neutralization, evaporation and filtration of the reaction mixture 28.5 parts of a pale yellowish oil of the formula

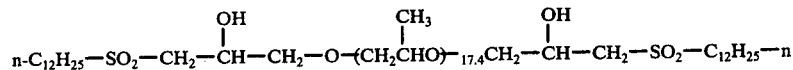

are obtained.

EXAMPLES 33 to 36

By use of other polypropylene glycols than that used in Example 32, the compounds of formula,

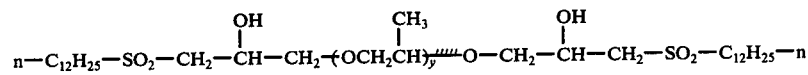

in which y″″″ is 5, 8, 12 and 20, respectively, are obtained in an analogous manner to the procedure described in Example 32. Each product is a colourless or pale yellowish, viscous oil.

EXAMPLE 37

In an analogous manner to the procedure described in Example 5, using n-octyl mercaptan in place of n-dodecyl mercaptan, and an appropriate polypropylene glycol, the compound of the following formula is obtained:

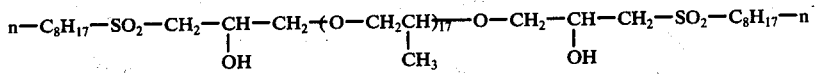

EXAMPLE 38

In an analogous manner to the procedure described in Example 1, using an appropriate polypropylene glycol in place of polyethylene glycol 300, the compound of the following formula is obtained:

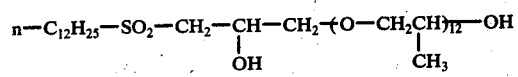

EXAMPLE 39

To 202g n-dodecyl mercaptan containing 1 g sodium hydroxide are added dropwise at 70°-80° 80g of 2,3-epoxy-1-propanol. The reaction mixture is then stirred for 2 hours at 85°-90°. With the temperature raised to 140°, 220 g of ethylene oxide are introduced over a period of 3 hours, and the reaction is allowed to proceed for a further hour.

To the reaction mixture is added 1 g of sodium hydroxide and, over a period of 6 hours with dropwise added at 140°-150°, 580 g of 1,2-propylene oxide. The reaction is allowed to proceed within the same temperature range for a further hour.

After cooling of the reaction mixture to 80°, 20 g of 85% formic acid, followed by 300 g of 34% hydrogen peroxide are added, the latter dropwise over the course of 3 hours. The temperature rises to 95°-100°, and the mixture is then stirred for a further 7 hours at about 100°. After cooling to 30°, 1of toluene is added immediately, the aqueous layer is separated, and the toluene solution is distilled in vacuo. The product consists of about 1000 g of a viscous, colourless oil of the formula:

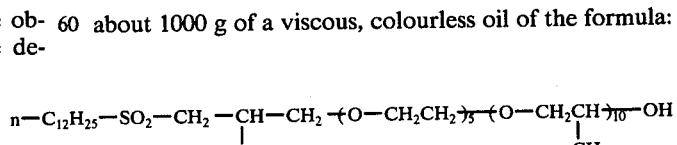

What is claimed is:
1. A compound of the formula,

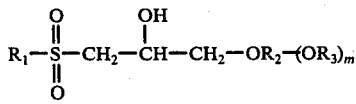

wherein R$_1$ is alkyl (C$_1$-C$_{22}$) or alkyl (C$_2$-C$_{22}$) containing 1 or 2 alkylenethioalkylene, alkylenesulphinylalkylene or alkylenesulphonylalkylene functions, any alkyl or alkylene being unsubstituted or substituted by —OH; cycloalkyl (C$_5$ or C$_6$) or alkyl (C$_1$-C$_6$) cycloalkyl (C$_5$ or C$_6$); or a radical —(R$_5$O)$\rightarrow$$_x$R$_4$, wherein R$_4$ is alkyl (C$_1$-C$_{22}$), phenyl, phenyl substituted by 1 or 2 alkyl (C$_1$-C$_{12}$) radicals, or phenylalkyl (C$_7$-C$_9$), each R$_5$ is, independently, —(CH$_2$)$_2$, —(CH$_2$)$_3$ or —CH(CH$_3$)CH$_2$— and $x$ is an integer 1 to 180, $m$ is an integer 1 to 7, R$_2$ is a group R$_{12}$, wherein R$_{12}$ is an ($m$ + 1) valent saturated aliphatic hydrocarbon (C$_2$-C$_{15}$) radical or an ($m$ + 1) valent saturated aliphatic hydrocarbon (C$_2$-C$_{15}$) radical containing 1 or 2 alkyleneoxyalkylene, alkylenethioalkylene, alkylenesulphinylalkylene or alkylenesulphonylalkylene functions; a bivalent radical of benzene, cyclohexane, biphenyl, diphenyloxide, diphenylsulphide, diphenylsulphoxide, diphenylsulphone, diphenylmethane, 2,2-diphenylpropane, bis-cyclohexylmethane or 2,2-bis-cyclohexylpropane, or a group R$_{12}$

wherein R$_{12}$ and R$_5$ are as defined above, $p$ is an integer 1 to 500, and $q$ is an integer 1 to ($m$ + 1), provided that when $q$ is greater than 1, each moiety in square brackets is independent of each other such moiety, and the total number, $y$, of radicals OR$_5$ does not exceed 500, and each R$_3$ has, independently, one of the significances of R$_1$ or is hydrogen, phenyl, naphthyl or phenylalkyl (C$_7$-C$_{12}$), or phenyl, naphthyl or phenylalkyl (C$_7$-C$_{12}$) substituted on the aromatic nucleus thereof by 1 to 3 alkyl (C$_1$-C$_{12}$), 1 cycloalkyl (C$_5$ to C$_{12}$), 1 or 2 alkoxy (C$_1$-C$_{18}$), 1 or 2 halogen, 1 phenyl and/or 1 phenoxy substituent, with 1 to 3 substituents and 1 to 18 carbon atoms in the aggregate thereof, a group

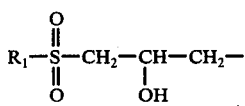

wherein R$_1$ is as defined above, or a group

wherein R$_6$ is alkyl (C$_1$-C$_{21}$), perfluoroalkyl (C$_3$-C$_{10}$), phenyl or naphthyl, or phenyl or naphthyl substituted by 1 to 3 halogen, 1 or 2 alkyl (C$_1$-(C$_{12}$) or 1 or 2 alkoxy (C$_1$-C$_{12}$) substituents, with 1 to 3 substituents and 1 to 18 carbon atoms in the aggregate thereof with the proviso that the sum of $x$ and $y$ is a maximum of 500.

2. A compound according to claim 1, of the formula,

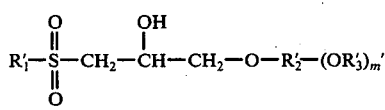

wherein R$_1$' is alkyl (C$_4$-C$_{18}$), alkylthioalkyl (C$_4$-C$_{18}$), alkylsulphonylalkyl (C$_4$-C$_{18}$) or alkylsulphonylalkyl (C$_4$-C$_{18}$), any of which is either unsubstituted or substituted by —OH; or a radical —(R$_5$O)$_x$'R$_4$' wherein R$_5$ is as defined in claim 1, R$_4$' is alkyl (C$_1$-C$_{22}$), benzyl, phenyl or alkyl (C$_1$-C$_{22}$), benzyl, phenyl or alkyl (C$_1$-C$_9$)-phenyl and $x'$ is an integer 1 to 100, $m'$ is an integer 1 to 5, R$_2$' is an ($m'$ + 1) valent saturated aliphatic hydrocarbon (C$_2$-C$_{10}$) radical, an ($m'$ + 1) valent alkylenesulphonylalkylene (C$_2$-C$_{10}$) radical, 4,4'-diphenyl sulphone, 4,4'-(2,2)-diphenyl propane or a radical —R$_5$-(OR$_5$)$_y$— wherein R$_5$ is as defined in claim 1, and $y'$ is an integer 1 to 300, and each R$_3$' has, independently, one of the significances of R$_1$' or is hydrogen, phenyl or benzyl, phenyl or benzyl substituted on the phenyl nucleus by 1 or 2 alkyl (C$_1$-C$_9$) or 1 alkoxy (C$_1$-C$_{18}$) substituent, a group

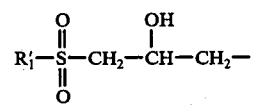

wherein R$_1$' is as defined above,

or a group wherein R$_6$' is alkyl (C$_9$-C$_{17}$), phenyl or phenyl substituted by alkyl (C$_1$-C$_9$) or chlorine, with the proviso that the sum of $x'$ and $y'$ is a maximum of 300.

3. A compound according to claim 2, of the formula,

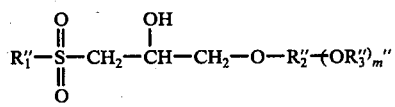

wherein R$_1$" is alkyl (C$_8$-C$_{18}$), $n$ is as defined in claim 1, $m''$ is an integer 1 or 2, R$_2$" is a divlent or trivalent saturated aliphatic hydrocarbyl (C$_2$-C$_6$) group or a group
—CH$_2$CH$_2$—(OCH$_2$CH$_2$)$_{y''}$.

wherein $y''$ is an integer 1 to 100 and each R$_3$" is, independently, hydrogen, alkyl (C$_8$-C$_{18}$) or a group

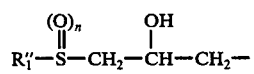

wherein R$_1$" is as defined above

4. A compound according to claim 3, of the formula,

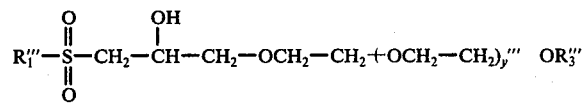

wherein R$_1$''' is alkyl (C$_9$-C$_{14}$), R$_3$''' is hydrogen or a group

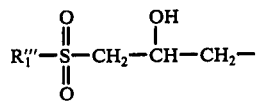

wherein $R_1'''$ is as defined above, $y'''$ is an integer 5 to 25.

5. A compound according to claim 2, of the formula,

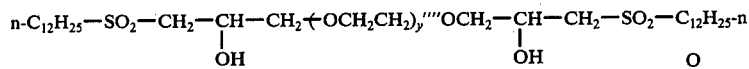

wherein $y''''$ is an integer 2 to 140.

6. A compound according to claim 4, of the formula,

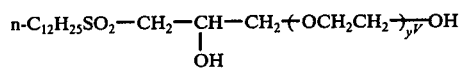

wherein $y^V$ is an integer 20 to 25.

7. A compound according to claim 1, of the formula,

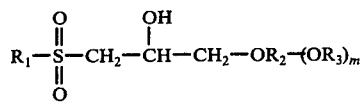

wherein $R_1$ is alkyl ($C_1$-$C_{22}$); alkyl ($C_1$-$C_{22}$) substituted by hydroxy; cycloalkyl ($C_5$ or $C_6$); or a radical $+R_5O+_xR_4$, wherein $R_4$ is phenyl substituted by 1 or 2 alkyl ($C_1$-$C_{12}$) groups and $R_5$ is $-(CH_2)_2$, $-(CH_2)_3$ or $-CH(CH_3)CH_2-$ and $x$ is an integer 1 to 180, $m$ is an integer 1 to 7, $R_2$ is a group $R_{12}$, wherein $R_{12}$ is an ($m + 1$) valent saturated aliphatic hydrocarbon ($C_2$-$C_{15}$) radical; an ($m + 1$) valent saturated aliphatic hydrocarbon ($C_2$-$C_{15}$) radical containing 1 or 2 alkylenesulphonylalkylene functions; diphenyl sulphone; 2,2-diphenyl propane; or 2,2-bis-cyclohexylpropane; or a group $R_{12}-[(OR_5)_p]_q$ wherein $R_{12}$ and $R_5$ are as defined above, $p$ is an integer 1 to 500, and $q$ is an integer 1 to ($m + 1$), provided that when $q$ is greater than 1, each moiety in square brackets is independent of each other such moiety, and the total number, $y$, of radicals $OR_5$ does not exceed 500, and each $R_3$ is, independently, hydrogen; alkyl ($C_1$-$C_{22}$); phenyl; phenyl substituted on the aromatic nucleus by 1 to 3 alkyl ($C_1$-$C_{12}$) groups; a group

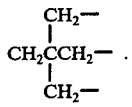

wherein $R_1$ is as defined above; or a group

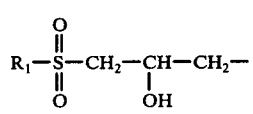

wherein $R_6$ is alkyl ($C_1$-$C_{21}$); perfluoroalkyl ($C_3$-$C_{10}$); phenyl; or phenyl substituted by 1 to 3 halo atoms or 1 or 2 alkyl ($C_1$-$C_{12}$) groups, with 1 to 3 substituents and 1 to 18 carbon atoms in the aggregate thereof, with the proviso that the sum of $x$ and $y$ is a maximum of 500.

8. A compound according to claim 7, of the formula,

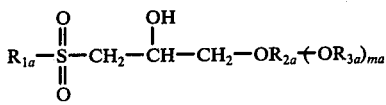

wherein $R_{1a}$ is alkyl ($C_1$-$C_{18}$); hydroxyethyl; cyclohexyl; or

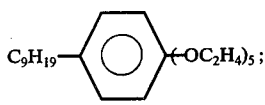

$R_{2a}$ is a group $R_{12a}$, wherein $R_{12a}$ is $-CH(CH_3)CH_2-$ $$\begin{array}{c} CH_2- \\ | \\ CH_2CCH_2- \\ | \\ CH_2- \end{array}$$

; $C_2H_4-SO_2-C_2H_4$; 4,4-diphenyl sulphone; 4,4'-(2,2)-diphenyl propane; 2,2-bis-cyclohexylpropane; or a group $R_{12b}-[(OR_{5a})_{pa}]_{qa}$ wherein $R_{12b}$ is $-(CH_2)_2$; $-CH(CH_3)CH_2-$; or 4,4'-(2,2)-diphenyl propane; $R_{5a}$ is $-(CH_2)_2$; or $-CH(CH_3)CH_2-$; $pa$ is an integer 1 or 135; and $qa$ is an integer 1 or 2, provided that when $qa$ is 2, each moiety in square brackets is independent of each other such moiety, and the total number, $y_a$, or radicals $OR_5$ does not exceed 136; $R_{3a}$ is hydrogen; alkyl ($C_{13}$-$C_{18}$), phenyl substituted on the aromatic nucleus by 1 to 2 alkyl ($C_4$-$C_9$) groups; a group

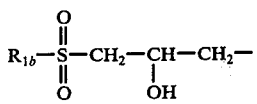

wherein $R_{1b}$ is alkyl ($C_4$-$C_{12}$); hydroxyethyl; or cyclohexyl; or a group

werein $R_{6a}$ is alkyl ($C_{11}$-$C_{17}$); perfluoroheptyl; phenyl; phenyl monosubstituted by t-butyl; or phenyl monosubstituted by halo; and $ma$ is an integer 1 to 3.

9. A compound of the formula,

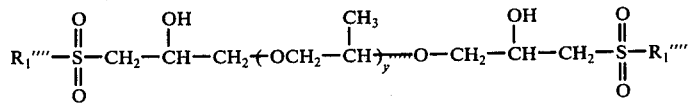

wherein $R_1''''$ is alkyl($C_4$-$C_{18}$), and $y''''$ is an integer 1 to 20.

10. A compound of the formula,

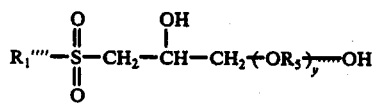

wherein $R_1''''$ is alkyl($C_4$-$C_{18}$), each $R_5$, independently, is —$(CH_2)_2$—, —$(CH_2)_3$— or —$CH(CH_3)CH_2$—, and $y''''$ is an integer 1 to 20.

11. A compound according to claim 3, of the formula,

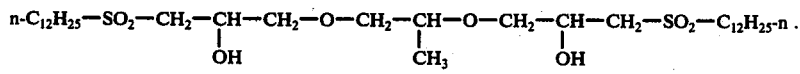

12. A mixture of compounds according to claim 9, wherein $R''''$ is n-$C_{12}H_{25}$ and the $y''''$'s have an average value of 17.4.

13. A compound according to claim 9, wherein $R''''$ is n-$C_{12}H_{25}$ and $y''''$ is 5, 8 12 or 20.

14. A compound according to claim 9, of the formula,

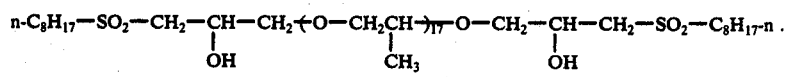

15. A compound according to claim 10, of the formula,

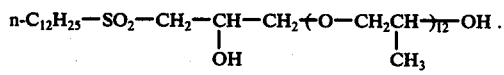

16. A compound according to claim 10, of the formula,

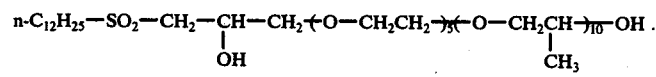

* * * * *